(12) United States Patent
Kouznetsov et al.

(10) Patent No.: US 9,804,084 B2
(45) Date of Patent: Oct. 31, 2017

(54) OPTICAL GAS SENSOR

(71) Applicant: Amphenol Thermometrics, Inc., Saint Marys, PA (US)

(72) Inventors: Andrian Kouznetsov, Goleta, CA (US); David B. Henderson, Goleta, CA (US); Daniel J. Gongloff, Goleta, CA (US)

(73) Assignee: AMPHENOL THERMOMETRICS, INC., Saint Marys, PA (US)

( * ) Notice: Subject to any disclaimer, the term of this patent is extended or adjusted under 35 U.S.C. 154(b) by 0 days.

(21) Appl. No.: 14/077,034

(22) Filed: Nov. 11, 2013

(65) Prior Publication Data

US 2015/0129767 A1 May 14, 2015

(51) Int. Cl.
*G01N 21/61* (2006.01)
*G01N 21/3504* (2014.01)
*G01N 21/03* (2006.01)

(52) U.S. Cl.
CPC ..... *G01N 21/3504* (2013.01); *G01N 21/0303* (2013.01)

(58) Field of Classification Search
CPC .................................................... G01J 5/0818
USPC .................................. 250/338.1, 341.1, 353
See application file for complete search history.

(56) References Cited

U.S. PATENT DOCUMENTS

| 3,810,302 | A | * | 5/1974 | Broers et al. | 29/600 |
| 3,950,980 | A | | 4/1976 | Braun et al. | |
| 3,997,786 | A | * | 12/1976 | Lauer et al. | 250/343 |
| 4,190,363 | A | * | 2/1980 | Adrian | G01N 21/05 |
| | | | | | 250/343 |
| 4,228,352 | A | * | 10/1980 | Adrian | 250/343 |
| 4,700,079 | A | * | 10/1987 | Ito | 250/574 |
| 5,060,508 | A | * | 10/1991 | Wong | 73/31.02 |
| 5,103,096 | A | * | 4/1992 | Wong | 250/343 |
| 5,424,718 | A | | 6/1995 | Muller et al. | |
| 5,696,379 | A | * | 12/1997 | Stock | 250/343 |
| 5,793,044 | A | | 8/1998 | Mace et al. | |
| 5,951,543 | A | * | 9/1999 | Brauer | 606/10 |
| 6,067,840 | A | | 5/2000 | Chevayohan et al. | |
| 6,527,398 | B1 | * | 3/2003 | Fetzer | 356/437 |
| 6,753,967 | B2 | * | 6/2004 | Stuttard | 356/437 |
| 7,214,939 | B1 | * | 5/2007 | Wong | G01J 3/108 |
| | | | | | 250/339.01 |
| 7,244,939 | B2 | * | 7/2007 | Stuttard | 250/343 |
| 7,259,374 | B2 | * | 8/2007 | Wong | 250/339.13 |
| 8,471,208 | B1 | * | 6/2013 | Tang | 250/343 |
| 8,720,040 | B2 | * | 5/2014 | Hongo et al. | 29/592.1 |
| 2002/0063216 | A1 | * | 5/2002 | Clausen et al. | 250/343 |
| 2004/0017975 | A1 | * | 1/2004 | Zheng | G02B 6/42 |
| | | | | | 385/43 |
| 2007/0145275 | A1 | | 6/2007 | Wong | |

* cited by examiner

*Primary Examiner* — David Porta
*Assistant Examiner* — Djura Malevic
(74) *Attorney, Agent, or Firm* — Blankrome LLP (57) ABSTRACT

A system includes a sensor body that has a folded optical waveguide configured in a "U" shape, wherein the waveguide is configured to convey infrared energy from one end of the waveguide to the other end of the waveguide.

25 Claims, 4 Drawing Sheets

OPTICAL GAS SENSOR

CROSS REFERENCE TO RELATED APPLICATION

This application is related to U.S. patent application Ser. No. 14/077,008, filed on Nov. 11, 2013, which is fully incorporated herein by reference and made a part hereof.

BACKGROUND

The subject matter disclosed herein relates to gas analysis and more specifically relates to an improvement in gas sampling and measurement/analysis.

Gas analysis sensors oftentimes utilize gas absorption of light to detect the presence and/or concentration of particular gases. For example, non-dispersive infrared ("NDIR") sensors measure the concentration of a particular gas in a sample by determining an absorption amount of particular wavelengths of light associated with a relatively-high level absorption band of the particular gas being measured.

As gas detection/analysis becomes more useful and NDIR sensors become less expensive and more popular, an increasingly vast number of applications for these sensors may be envisioned. For flexibility and/or cost savings, it may be desirable to reduce the size of the NDIR sensors. However, NDIR sensor accuracy may be directly impacted by the gas sample size that resides between an infrared source and an infrared detector. Unfortunately, traditional NDIR sensor designs have had to balance between sensor size reduction and sensor accuracy because reducing the size of NDIR sensors has traditionally resulted in a greatly reduced gas sample size, thus potentially reducing accuracy of the NDIR sensors.

Accordingly, it would be beneficial to provide an enhanced sensor design that provides for increased gas sampling while reaping the benefits of a reduced form factor. This and further objects and advantages will be apparent in the detailed description of embodiments discussed below.

BRIEF DESCRIPTION

Embodiments of the current disclosure use enhanced designs of a shaped waveguide to provide reduced manufacturing costs, and/or increased accuracy for size-reduced gas sensors.

In one embodiment, a system includes a sensor body that has a folded optical waveguide configured in a "U" shape, wherein the waveguide is configured to convey infrared energy from a first end of the waveguide to a second end of the waveguide.

In a second embodiment, a sensor includes a sensor body. The sensor body includes a top-portion having a first recess and a bottom-portion having a second recess configured to mate with the first recess. The sensor body also includes at least one cavity providing an aperture between an outside surface of the sensor body to the first recess, to the second recess, or both; an infrared source inlet configured to receive an infrared source; and an infrared source inlet configured to receive an infrared source. The sensor also includes an infrared detector inlet configured to receive an infrared detector; an infrared detector disposed in the infrared detector inlet of the sensor body. When mated, the first recess and the second recess form a waveguide configured to carry energy emitted from the infrared source to the infrared detector.

In a third embodiment, a method comprises detecting a presence or a concentration of gas using a sensor having a sensor body that includes a top-portion having a first recess and a bottom-portion having a second recess configured to mate with the first recess. The sensor body also includes at least one cavity providing an aperture between an outside surface of the sensor body to the first recess, to the second recess, or both; an infrared source inlet configured to receive an infrared source; and an infrared source inlet configured to receive an infrared source. The sensor also includes an infrared detector inlet configured to receive an infrared detector; an infrared detector disposed in the infrared detector inlet of the sensor body. When mated, the first recess and the second recess form a waveguide configured to carry energy emitted from the infrared source to the infrared detector.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Figure 1:
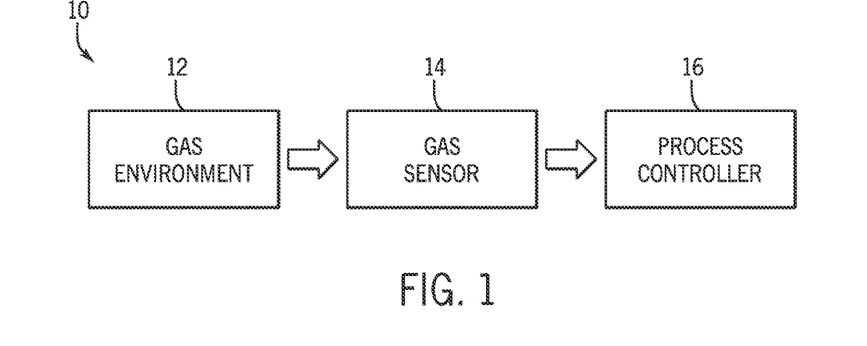
FIG. 1 illustrates a process for gas measurement using an enhanced gas sensor, in accordance with an embodiment.

Turning now to the drawings and referring first to FIG. 1, an embodiment of a process 10 for gas measurement using an enhanced gas sensor is provided. A gaseous environment 12 may include one or more gases to be measured. For example, a particular gaseous concentration in an environment 12 may trigger one or more process controls effecting a change in the environment 12 or elsewhere.

In one example, an environment 12 affected by a heating, ventilation, and air-conditioning (HVAC) system may be altered based upon the presence of a particular gas. For instance, carbon-dioxide levels in the environment 12 may indicate a particular number of humans in the environment 12, because the carbon-dioxide levels may be attributed to the breathing functions of humans, thus providing an indication of a number of humans within the environment 12. This indication may impact control of the HVAC system. For example, if the indicator suggests that few people are in the environment 12, the HVAC system may respond in a less sensitive manner than situations where the indicator suggests that a large number of people are in the environment 12, resulting in operation cost savings.

To obtain an accurate indication, an enhanced gas sensor 14 may collect information indicative of a particular gas concentration within the environment 12. In the HVAC example, information relating to the carbon dioxide concentration in the environment 12 may be observed by the enhanced gas sensor 14. As will be discussed in more detail below, the enhanced gas sensor 14 may be designed such that manufacturing costs of the enhanced gas sensor 14 are reduced (e.g., via simplified manufacturing of a two-piece body assembly of the enhanced gas sensor 14). Further, increased cohesion between sensor size reduction and sensor accuracy may be obtained (e.g., due to an enhanced waveguide design that allows for an increased gas sample size in a reduced enhanced gas sensor 14 form factor). The enhanced gas sensor 14 may provide a sensor signal to a process controller 16, indicating the presence and/or concentration of a gas in the environment 12. Accordingly, as the process controller 16 becomes aware of the presence of the gas and/or the gaseous concentration, the process controller 16 may affect one or more controlled processes. In the provided HVAC example, an HVAC controller may define a particular thermostat sensitivity of the HVAC system based up an estimated number of humans in the environment 12, as indicated by the gas presence and/or concentration. Accordingly, use of the enhanced gas sensor 14 may result in increased efficiencies and/or reduced operating costs.

In one embodiment, the enhanced gas sensor 14 may include a number of input/output (I/O) connectors (e.g., pins, terminals, and the like) useful in providing for a communicative connection to various external systems, such as microcontrollers, external circuitry, other sensors, and so on. The techniques described herein may use a single pin (or multiple configuration pins) as a configuration pin or pins suitable for receiving data useful in reconfiguring the enhanced gas sensor 14. For example, certain data may be communicated to a configuration pin and the enhanced gas sensor 14 may change functionality based on the transmitted data. Indeed, rather than assigning a single function to a specific pin or pins, the pins may be each be capable of providing multiple functions, and a specific function may be chosen dynamically via the configuration pin or pins. Accordingly, a smaller number of pins may be used, suitable for supporting any number of enhanced gas sensor 14 configurations. It is to be noted that the enhanced gas sensor 14 may be disposed in a variety of applications, including HVAC systems, rebreather systems (e.g., closed circuit and/or open circuit rebreather systems useful in providing breathing gas to a human), medical systems, industrial systems, and so on.

Figure 2:
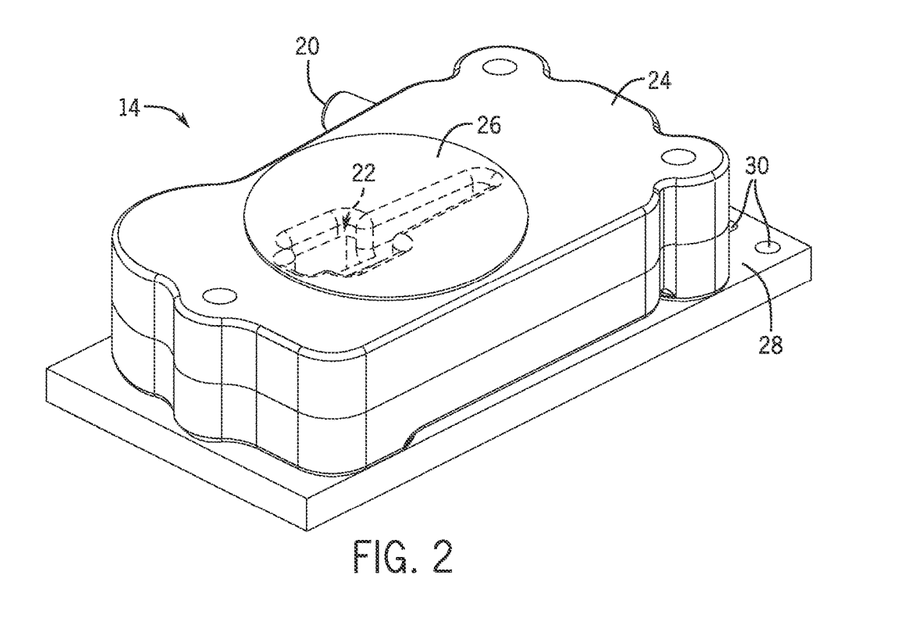
FIG. 2 illustrates a perspective view of the enhanced gas sensor of FIG. 1, in accordance with an embodiment.

FIG. 2 illustrates a perspective view of the enhanced gas sensor 14 of FIG. 1, in accordance with an embodiment. As mentioned above, the enhanced gas sensor 14 may include a small form factor (e.g., approximately 2.5 cm L×1.5 cm W×0.5 cm H), while allowing for an increased gas sample size. In the provided embodiment, the enhanced gas sensor 14 may receive a gas sample via a gas inlet port 20 and/or one or more openings (e.g., cavity 22) in the sensor body 24 that access an internal gas pathway of the enhanced gas sensor 14.

When reducing the form factor size of an NDIR sensor (e.g., enhanced gas sensor 14), particular difficulties may arise with regard to assuring a proper ventilation rate of ambient air through the enhanced gas sensor 14, while protecting the sensor from environmental externalities (e.g., dust and/or moisture). In the current embodiment, the cavity 22 is represented by dashed lines, because the cavity 22 is disposed beneath a filter 26, which may serve to block dust and moisture from entering an internal portion of the enhanced gas sensor 14. Ambient air may more quickly diffuse through the filter 26 into the cavity 22, due to the relatively large filter surface area. For example, the filter surface area may be approximately 1.33 cm$^2$. As will be discussed in more detail below, the ambient air (e.g., an ambient air sample) may flow through the cavity 22 into an internal passageway within the enhanced gas sensor 14 and flow out of the cavity 22 via a convection process.

As the air flows through the internal passageway, it may be analyzed for concentrations of particular gases. For example, the sensor body 24 may be coupled to a printed circuit board (PCB) 28 that provides a controlled infrared source (e.g., a tungsten filament light bulb, light-emitting diode, a thermoelectric microelectromechanical system (MEMS) device, a laser, etc.) and detector (e.g., thermopile, etc.) pair. Analysis of infrared characteristic affected by the air sample obtained using the infrared source and detector pair may be beneficial in determining a gaseous concentration in the air sample. As will be described in more detail below, the infrared source and detector pair may be controlled via commands provided via connectors (e.g., connector terminals or connector pins) 30 of the PCB 28. Once characteristics have been read by the infrared detector, the detector readings and/or analysis data resulting from the detector readings may be provided as an output of the enhanced gas sensor 14 via the connector pins 30 of the PCB 28.

Figure 3:
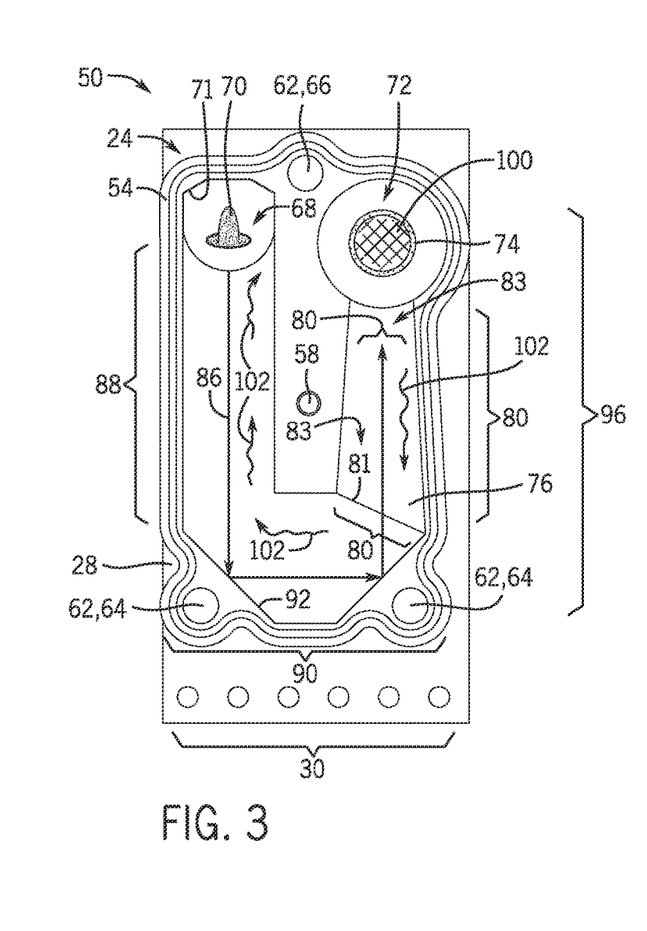
FIG. 3 illustrates a top-view of a manufactured bottom-half of an enhanced gas sensor body, in accordance with an embodiment.
Figure 4:
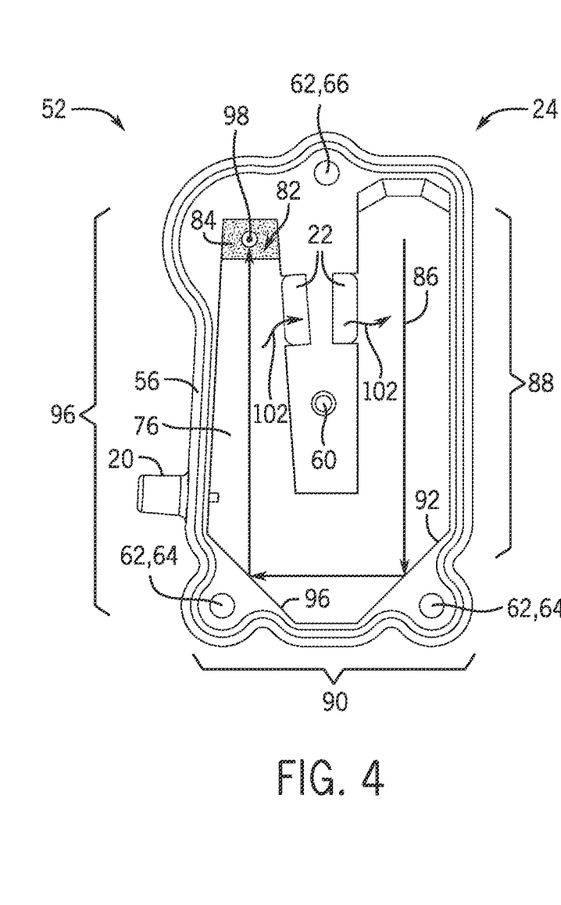
FIG. 4 illustrates a bottom-view of a manufactured top-half of an enhanced gas sensor body, in accordance with an embodiment.

Having now described the basic function of the enhanced gas sensor 14, the discussion now turns to mechanical design and mounting of the enhanced gas sensor 14. To improve manufacturability and/or assembly of NDIR sensors (e.g., enhanced gas sensor 14 of FIG. 2), the sensor may be an assembly of two pieces. FIG. 3 illustrates a top-view of a manufactured bottom-half 50 of an enhanced gas sensor body (e.g., sensor body 24 of FIG. 2), in accordance with an embodiment, and FIG. 4 illustrates a bottom-view of a manufactured top-half 52 of an enhanced gas sensor body 24, in accordance with an embodiment. That is, FIGS. 3 and 4 illustrate interior views when the halves 50 and 52 are disposed onto their "backs" and viewed from the top, showing the illustrated features. Because these pieces are designed to mate with one another and mount to a common printed circuit board (PCB), the pieces will be first briefly described together followed by a more detailed description of particular features of each piece. Further, while the embodiments provided in FIGS. 3 and 4 will be discussed as two pieces with equal thicknesses (e.g., two halves 50 and 52 of the enhanced gas sensor 14), which is believed to provide enhanced manufacturability and stability, alternative embodiments may include pieces that form a mating line not directly through the center of the fully assembled enhanced gas sensor 14 (e.g., are not equal halves).

The two pieces depicted in FIGS. 3 and 4 may be coupled to one another with a set of interlocking features that create dust and moisture barriers along the mating line as well as provide for simplified assembly by providing mating guides and reducing reliance on adhesive or other sealing materials at the mating line. For example, bottom-half 50 includes a self-aligning tongue 54 that is designed to mate with groove 56 of the top-half 52. In alternative embodiments, the bottom-half 50 may include a self-aligning groove designed to mate with a tongue of the top-half 52. Further, the two pieces may include additional mating features, such as one or more shear joints, step joints, butt joints, and/or pin and hole features that may provide dust and/or moisture barriers and/or may eliminate or reduce lateral movement between the halves 50 and 52. In the illustrated embodiment, a hole 58 and pin 60 are placed centrally to reduce lateral movement of the bottom-half 50 and top-half 52 when coupled. The hole 58 and pin 60 are designed to mate with one another as the bottom-half 50 and top-half 52 are mated.

The sensor body 24, which is made up of bottom-half 50 and top-half 52 is designed to mount to the PCB 28 as illustrated in FIG. 3. In some embodiments, a mounting system (e.g., three-point mounting system 62) may be used to mount the bottom-half 50 to the PCB 28. Further, the mounting system may be used to mount the top-half 52 to the bottom-half 50, forming a complete sensor body 24. As mention above the tongue 54 is designed to mate with the groove 56. When mated, a fastening mechanism may fix the bottom-half 50 and top-half 52 (e.g., via a screw that is provided through each point in the mounting system (e.g., each point in the three-point mounting system 62).

In a three-point mounting system 62 configuration, the three-point mounting system 62 may be in a configuration such that one end of the sensor body includes two corner mounts 64 and the other end of the sensor body includes a single central mount 66. In alternative embodiments, the mounting system may include a different placement of mounts or a different number of mounting points may be used.

However, using the three-point mounting system 62 may result in enhanced mechanical stability between the PCB 28 and the sensor body 24. Further, stress transfer between the PCB 28 and the sensor body 24 may be reduced using the three-point mounting system 62. In certain embodiments, the sensor body 24 may be elevated from the PCB 28 except at the three-point mounting system 62. This may result in more PCB real-estate (e.g., between the elevated portion of the sensor body 24 and the PCB 28). In alternative embodiments, the entire sensor body 24 or an alternative portion of the sensor body 24 may be mounted flat to the PCB 28.

Regardless of the number of points in the mounting system, the sensor body 24, or the portion of the sensor body 24 that is mounted flat to the PCB 28, a mechanical fastener (e.g., a screw) may be used at the mounting points to mount the sensor body 24 to the PCB 28. This may lead to added efficiencies, such as mechanical and manufacturing efficiencies by relying less on the use of adhesives in mounting the sensor body 24 to the PCB 28. However, in certain embodiments, alternative fastening mechanisms such as epoxy or ultrasonic welding may join the bottom-half 50 with the top-half 52 and provide a connection between the sensor body 24 and the PCB 28 via screws, heat stake, swaging and forming, and/or the use of adhesives.

Having discussed the basic mechanical design of the sensor body 24 and mounting of the sensor body 24 to the PCB 28, the discussion turns to a more detailed look at operation of the enhanced gas sensor 14. As illustrated, in FIG. 3, the bottom-half 50 may include an infrared source inlet 68 that is designed to accept an infrared source (e.g., light source) 70 disposed on the PCB 28. Further, the bottom-half 50 includes an infrared detector inlet 72 designed to accept an infrared detector (e.g., light detector) 74 disposed on the PCB 28. Further, bottom-half 50 and top-half 52 each include shaped (e.g., "U" shaped) recesses 76 that form a shaped (e.g., "U" shaped) waveguide 78 when the bottom-half 50 and top-half 52 are mated. The infrared source 70 is located at one end of the shaped waveguide 78 and the infrared detector 74 is located at the other end of the shaped waveguide 78. As illustrated, the shaped waveguide 78 is designed with a folded shape (e.g., a "U" shape). Further, cross-sections of the shaped waveguide 78 may be rectangular, square, hexagonal, octagonal, circular, or any other shape. Further, a portion (e.g., portion 80) of the shaped waveguide 78 may be tapered, as illustrated at line 82, to form a tapered optical cone 81 with a narrow portion 83 of the cone 81 facing the infrared detector 74. This optical cone 81 may ensure an optimal optical irradiance from the infrared source 70 to the infrared detector 74 along the shaped waveguide 78.

As illustrated in FIGS. 3 and 4, the infrared source 70 provides radiation 86 at a first section 88 of the shaped waveguide 78. The bottom-half 50 and top-half 52 may be formed from a plastic that is coated with a reflective material, such as gold. The use of the reflective material may ensure energy retention and proper energy redirection using angled walls within the sensor body 24. For example, in some embodiments, an optical mirror similar to optical mirror 84 (discussed below) may be included where the optical axis of the infrared source 70 is perpendicular to the optical axis of the shaped waveguide 78. When flat, the reflecting mirror may be oriented at a 45 degree angle, thus resulting in a 90 degree redirection of energy. However, in some embodiments, when the mirror is not flat (e.g. is an oval shape), the mirror may be oriented at a different angle (e.g., +/−30 degrees).

Additionally, in some embodiments, a collimating reflector 71 may collect and direct optical energy (e.g., radiation 86) from the source 70 into the direction of the detector 74. The shape and/or presence of the collimating reflector 71 and/or the shape of the first section 88 may vary based upon on a configuration of the infrared source 70. For example, when a microelectromechanical system (MEMS) and/or solid state infrared sources are used, an additional optical cone similar to optical cone 81 may be disposed in first section 88 of the shaped waveguide 78.

Once the radiation 86 has reached the end of the first section 88, the radiation 86 is reflected to a second section 90 of the shaped waveguide 78 via a reflective wall 92 and is then reflected to a third section 94 via a reflective wall 96. Upon reaching the reflective mirror 84, the radiation is directed towards the optical axis of the infrared detector 74 as illustrated by symbol 98. The infrared detector 74 may include a bandpass filter 100 that excludes high and low range wavelengths (e.g., wavelengths outside the range of about 2-6 micrometers) of radiation 98 from passing to the infrared detector 74. Accordingly, the wavelength range accepted by the infrared detector 74 may be controlled by the filter 100, such that wavelength ranges which are particularly affected by the target gas may be detected and/or analyzed.

The optical axis of the infrared detector 74 (e.g., the plane where light enters the infrared detector 74) may be disposed perpendicular to the optical access of the shaped waveguide 78. Accordingly, a reflecting mirror 84 may be disposed within the sensor body 24 (e.g., on the top-half 52) that may be used to direct radiation from the infrared source 70 that reaches the mirror 84 to the perpendicular optical axis of the infrared detector 74. In some embodiments, the mirror 84 may include a scattering feature 85 that may be used to reduce sensitivity to mechanical instabilities by scattering the energy at the surface of the detector 74. As above, when flat, the reflecting mirror 84 may be oriented at a 45 degree angle, thus resulting in a 90 degree redirection of energy. However, in some embodiments, when the mirror 84 is not flat (e.g. is an oval shape), the mirror 84 may be oriented at a different angle (e.g., +/−30 degrees).

In some embodiments, the optical axis of the infrared detector 74 may be aligned with the shaped waveguide 78 optical axis. In such an embodiment, the mirror 84 may not be necessary, because the energy would not need to be re-directed.

The use of the infrared source 70 generates thermal differences between the infrared source 70 end of the shaped waveguide 78 and the infrared detector 74 end of the shaped waveguide 78. Accordingly, as illustrated by the arrows 102, as ambient air travels through the filter 26 of FIG. 2 through the cavity 22, the air may move via a convection flow created by the thermal differences. Because the infrared source 70, the infrared detector 74, and the cavity 22 are located close to the ends of the shaped waveguide 78, rapid and complete air exchange between the shaped waveguide 78 and the cavity 22 may occur. This efficient ventilation may result in increased sensor accuracy by maintaining a fresh gas sample.

Figure 5:
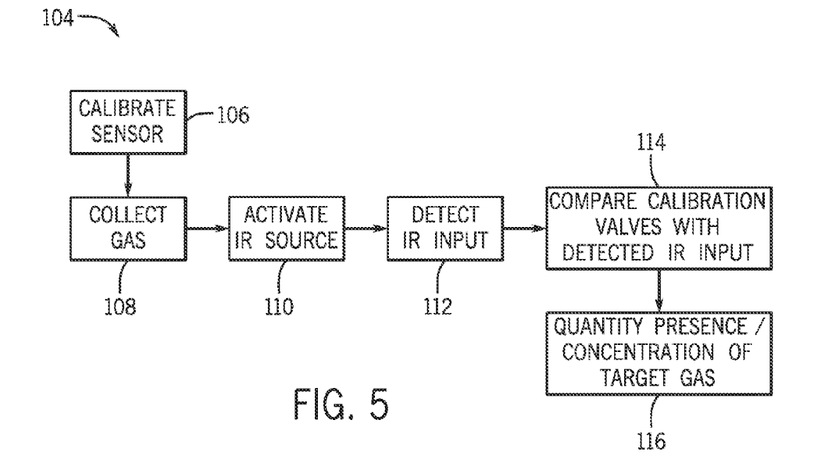
FIG. 5 illustrates a process for measuring gas via the enhanced gas sensor, in accordance with an embodiment.

Turning now to an operational discussion of the enhanced gas sensor 14, FIG. 5 illustrates a process 104 for measuring gas via the enhanced gas sensor 14, in accordance with an embodiment. The enhanced gas sensor 14 may be calibrated (block 106). For example, a measurement of energy from the infrared source that reaches the detector 74 without being affected by the presence of the target gas may be recorded. This measurement may take into account the reflective qualities of the shaped waveguide 78, the light source configuration (e.g., type, emitted wavelengths, etc.), and/or the detector 74 configuration (e.g., the filter configuration).

Once the enhanced gas sensor 14 has been calibrated, a sample is collected from the gas environment 12 (block 108). For example, gas may be collected through gas inlet port 20, cavity 22 disposed on the top of the sensor body 24, and/or one or more cavities disposed on a side or the bottom of the sensor body 24. As mentioned above, the collected air may flow in through the cavity 22 and/or other cavities, travel along the shaped waveguide 78 and ventilate out of the cavity 22 and/or other cavities via natural conduction caused by differing temperatures at each end of the shaped waveguide 78 and/or cavity 22 and/or other cavities. As the air flows through the shaped waveguide 78, the air may be analyzed for the presence and/or concentration of a target gas.

To analyze the air, the infrared source 70 is activated (block 110). As discussed above, the energy (e.g., radiation) emitted by the infrared source 70 flows along the shaped waveguide 78 sections 88, 90, and 94 to reach the infrared detector 74. As the energy passes through the shaped waveguide 78, the energy may be affected by the presence of the target gas. For example, a portion of the energy may be absorbed by the target gas. Accordingly, the amount of energy measured as reaching the detector 74 during the calibration step may differ from the amount of energy that reaches the detector 74 with the presence of the target gas. Accordingly, upon detecting the amount of energy that reaches the detector 74 (block 112), the detected amount of energy may be compared with the calibration measurement to determine an amount of energy that has been lost (block 114). Next, the determined amount of energy that has been lost is used to quantify the presence and/or concentration of the target gas in the air (block 116). The activation (block 110) of the infrared source 70 may be performed on a modulated basis by turning on the source 70 for a desired period of time, then turning off the source 70 for another period of time, turning back on the source 70, and so on.

Figure 6:
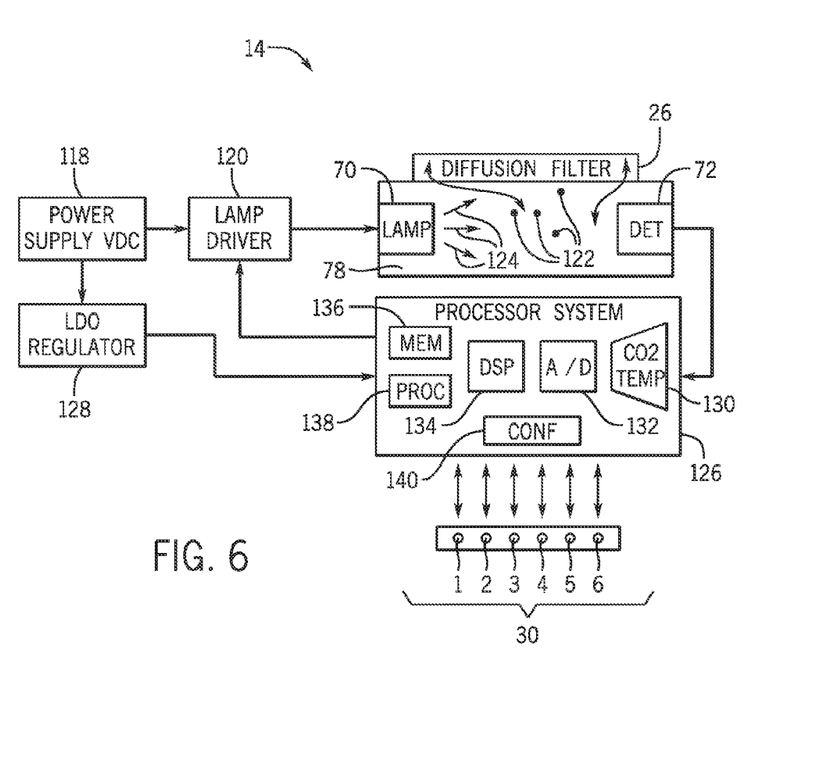
FIG. 6 is a block diagram including certain systems of the enhanced gas sensor of FIG. 1, in accordance with an embodiment.

Turning now to FIG. 6, the figure is a block diagram illustrating certain systems of the enhanced gas sensor 14, in accordance to one embodiment. In the depicted embodiment, a power supply 118 is conductively coupled to a lamp driver 120. The power supply 118 may provide, for example, electric power having a direct current voltage (VDC) in a range suitable for operating the light source (e.g., infrared source) 70, such as a range between 3 and 10 VDC. Accordingly, the lamp driver 120 may modulate (e.g., turn on and off) the light source 70 at certain desired intervals useful in more accurately observing gas 122 (e.g., CO2) disposed inside of the shaped waveguide 78. As mentioned above, the filter 26 may provide for filtering of particles, such as dust, but enable the diffusion of gas 122 into the shaped waveguide 78. Light 124 produced by the light source 70 may then traverse through the shaped waveguide 78 and impinge onto the detector 74. The detector 74 may then produce a signal correlative with an amount of the gas 122, and the signal may then be transmitted to a processing system 126.

Electric power used by the processing system 126 may be provided, for example, by a low-dropout (LDO) voltage regulator 128 electrically coupled to the power supply 118. The LDO voltage regulator 128 may enable a small input-output differential voltage, thus providing for output voltage to drive the processing system 126 in a more efficient manner. For example, the LDO regulator may provide a lower operating voltage, a higher operation efficiency, and a lower heat dissipation, thus improving the overall energy of operations for the enhanced gas sensor 14.

The processing system 126 may receive the signal transmitted by the detector 74 and transform the signal into data representative of the amount of gas 122 detected. In the depicted embodiment, the processing system 126 may include a gas (e.g., CO2) temperature sensor 130, an analog to digital (A/D) system 132, a digital signal processing (DSP) system 134, a memory 136, and a processor 138. The processing system 126 may also include an I/O reconfiguration system 140 useful in dynamically reconfiguring how the enhanced gas sensor 14 drives the I/O pins 30, as described in more detail below.

In use, the signal transmitted via the detector 72 may be transformed by taking into account gas temperature (e.g., gas temperature measured via temperature sensor 130), and processed by the A/D system 132 and the DSP system 134 to arrive at, for example, a digital data representative of an amount of gas sensed by the enhanced gas sensor 14. The A/D system 132 may be used to convert analog signals into digital data, while the DSP system 134 may be used to process the digital data (e.g., stream of digitally encoded values) by filtering, applying certain techniques (e.g., Fourier transforms, z-plane analysis, wavelet analysis, and so on), and then calculating the amount of gas sensed. In one example, the memory 136 may store computer executable code or instructions, including gas quantity equations, calibration values, calibration equations, and the like, that may be executed by the processor 138 to derive the amount of gas sensed. Indeed, the memory 136 may store computer code or instructions implementing all of the processes described herein, such as the processes in FIGS. 5 and 7, and the processor 138 may execute said code.

The reconfiguration system 140 may be suitable for dynamically reconfiguring the sensor's I/O pins 30. For example, pin 6 may be selected as the pin to be used to choose functionality associated with the remaining pins 1, 2, 3, 4, and 5. Accordingly, the pin 6 may measure voltage, load (e.g., resistance or current), or a combination thereof, and the reconfiguration system 140 may then apply the measurements to change how the remainder of the I/O pins 1-5 operate. The selection of desired functionality (e.g., sensor functions) may occur, for example, on power up of the enhanced gas sensor 14, on a desired schedule or cycle (e.g., every 10 seconds, every minute, every 5 minutes, every 10 minutes, every hour), at a desired time of sensor operation (e.g., after 10 seconds of operation, after one minute of operation, after 5 minutes of operation, after 10 minutes of operation, after an hour of operation), when initiated by a command received by the reconfiguration system 140 (e.g., a command received from an external system via one or more of the I/O pins 1-5), or a combination thereof. The reconfiguration system 140 may be provided as hardware (e.g., as an application specific integrated circuit [ASIC], field-programmable gate array [FPGA], custom chip, or other circuitry), as software executable via the processor 138 and stored in the memory 136, or as a combination thereof.

While any number of sensor functions may be selected via voltage and/or load indications communicated to pin 6, Table 1 below lists three different sensor functions as follows:

TABLE 1

| | Indication to Pin 6 | | |
|---|---|---|---|
| Connector pin out | 10 kOhm to GND Sensor Function 1 | V−, GND Sensor Function 2 | V+, Power Sensor Function 3 |
| 1 | TxD (UART) | I2C_SDA | Threshold 3 output |
| 2 | RxD (UART) | I2C_CSL | Threshold 2 output |
| 3 | V+, POWER | V+, POWER | V+, POWER |
| 4 | V−, GND | V−, GND | V−, GND |
| 5 | PWM 1 | PWM 2 | Threshold 1 output |
| 6 | output controlling flow for ModBus transceiver | CONFIG Input setting configuration 2 | CONFIG Input setting configuration 3 |

For Sensor Function 1, the indication provided to pin 6 consists of a load, such as a 10 k Ohm load. Accordingly, the reconfiguration system 140 may configure the sensor 14 so that a universal asynchronous receiver/transmitter (UART) protocol, including an UART protocol suitable for communications via a ModBus transceiver, is used. Thus, pin 1 is configured to provide for UART transmission, pin 2 is configured to provide for UART reception, pin 3 is configured to couple to positive voltage, pin 4 is configured to couple to negative voltage or ground, and pin 5 is configured to provide pulse width modulation (PWM) data communications.

For Sensor Function 2, the indication provided to pin 6 consists of a negative voltage or ground. Accordingly, the reconfiguration system 140 may set up the sensor 14 so that an Inter-Integrated Circuit, referred to as I-squared-C, I-two-C, or I2C, is used. Thus, pin 1 is configured to provide for I2C transmission via the serial data line (SDA), pin 2 is configured to provide for I2C reception via the clock line, pin 3 is configured to couple to positive voltage, pin 4 is configured to couple negative voltage or ground, and pin 5 is configured to provide pulse width modulation (PWM) data communications.

For Sensor Function 3, the indication provided to pin 6 consists of a positive voltage. Accordingly, the reconfiguration system 140 may configure the sensor 14 so that threshold output signals are provided. That is, the sensor 14 may now communicate signals representative of a gas amount threshold having been crossed or exceed. Thus, pin 5 is configured to provide for a first signal when a first threshold is exceeded, pin 2 is configured to provide for a second signal when a second threshold is exceeded, pin 3 is configured to couple to positive voltage, and pin 4 is configured to provide for a third signal when a third threshold is exceeded. It is to be noted that while three sensor functions are described, any number of functions may be provided, including functions where the I/O pins 30 are used to provide for Foundation Fieldbus communications, HART communications, and so on. By providing for reconfiguration of the I/O pins 30, the techniques described herein may minimize pin count while increasing the types of communications that may be provided by the pins 30. Indeed, rather than assign a set of pins 30 to each sensor function listed in Table 1, possibly resulting in eighteen pins (e.g., six pins times three functions), the techniques described herein may provide the same functionality with six pins. The techniques described herein may also be applicable to other sensors sensing environmental conditions, such as humidity sensors, temperature sensors, pressure sensors, flow rate sensors, chemical sensors, clearance (e.g., distance between a moving and a stationary component) sensors, vibration sensors, speed sensors, and the like.

Figure 7:
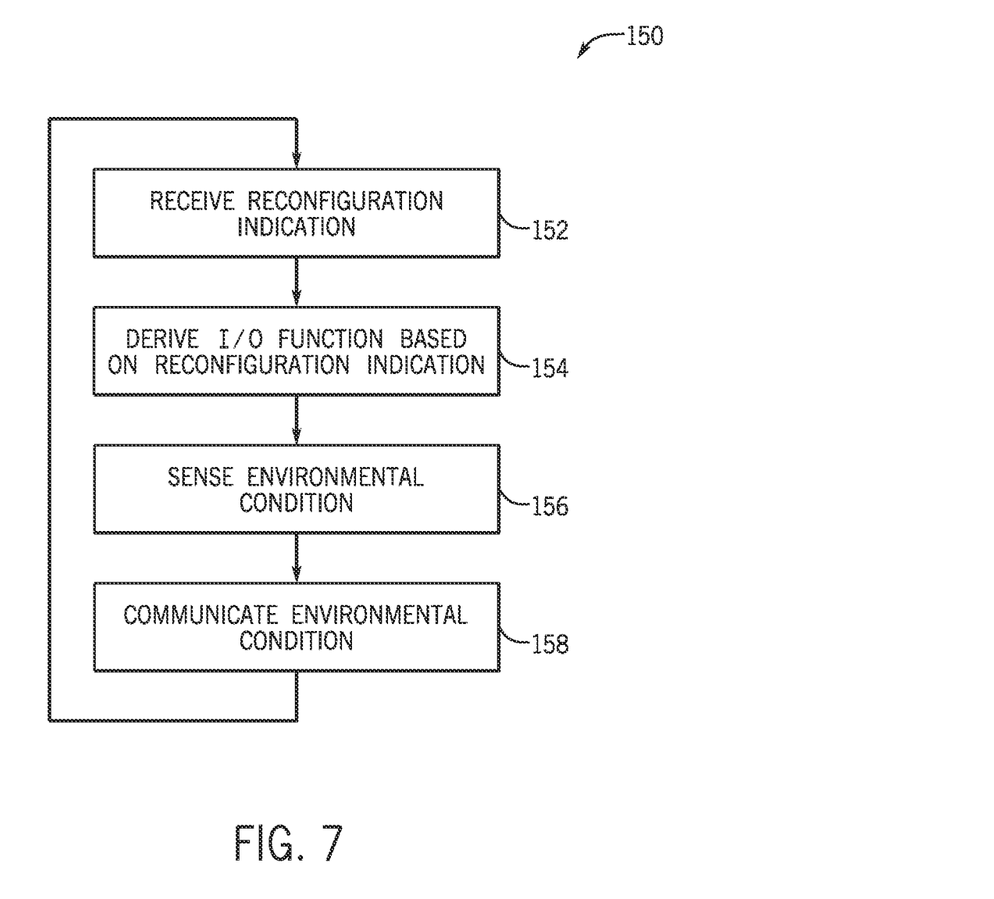
FIG. 7 illustrates a process for reconfiguration of input/output (I/O) connectors of the enhanced gas sensor of FIG. 1.

Turning now to FIG. 7, the figure is a flowchart illustrating a process 150 suitable for reconfiguring the I/O connectors 30 shown in FIG. 6 above. The process 150 may be implemented as computer executable code stored in the memory 136 and executed by the processor 138 of the sensor 14. The process 150 may receive a reconfiguration indication (block 152), for example via a voltage and/or load communicated to pin 6. Based on the indication, the process 150 may then derive one or more of the sensor functions (block 154), such as the functions listed in Table 1 above. As mentioned previously, the indication to reconfigure the I/O pins may occur on power up of the sensor 14, on a desired schedule or cycle (e.g., every 10 seconds, every minute, every 5 minutes, every 10 minutes, every hour), at a desired time of sensor operation (e.g., after 10 seconds of operation, after one minute of operations, after 5 minutes of operations, after 10 minutes of operations, after an hour of operations), when initiated by a command received by the reconfiguration system 140 (e.g., a command received from an external system via one or more of the I/O pins 1-5), or a combination thereof.

The sensor 14 may then sense environmental conditions, such as an amount of a gas (e.g., CO2) present (block 156). For example, the sensor 14 may apply the process 104 of FIG. 5 to measure an amount of the gas. Data representative of the environmental condition, or any other data, may then be communicated (block 158) to any number of external systems communicatively coupled to the sensor 14 via the I/O pins 30. The external systems (e.g., HVAC systems, rebreathers, industrial systems, industrial controllers, chemical systems, medical systems) may then further process the sensor data for use in control algorithms and the like. By providing for reconfigurable I/O pins 30, the techniques describe herein may minimize pin size and/or connector size while improving sensor flexibility.

Technical effects of the embodiments described herein include maintaining accuracy while reducing the size of NDIR sensors. Additionally, technical effects include reconfiguration of I/O connectors suitable for providing for a variety of sensor functions with minimal pin count. Further, these embodiments provide simplified sensor manufacturing processes, resulting in reduced manufacturing costs.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A sensor, comprising:
a sensor body having a first end and an opposing second end;
a folded optical waveguide positioned within the sensor body and configured in a "U" shape having a first section, a second section, and an intermediate portion joining the first section and the second section, wherein the waveguide is con d to convey infrared energy from a first end of the waveguide to a second end of the waveguide, and
wherein the second section of the waveguide is tapered along its entire length extending between the first end of sensor body and the opposing second end of the sensor body.

2. The sensor of claim 1, comprising:
an infrared source inlet at the first end of the waveguide; and
an infrared detector at the second end of the waveguide.

3. The sensor of claim 2, comprising:
one or ore cavities disposed proximate to the first and second ends such that a convection may create an airflow along the waveguide for air flowing through the one or more cavities.

4. The sensor of claim 1,
wherein the first section is connected to the intermediate section by a first reflecting wall and the intermediate section is connected to the second section by a second reflecting wall,
wherein the first reflecting all is configured to direct energy propagating through the first section to the intermediate section, and
wherein the second reflecting all is configured to direct energy propagating through the intermediate section to the second section.

5. The sensor of claim 4, wherein an infrared source inlet is disposed at the first end of the waveguide, and wherein an infrared detector inlet is disposed at the second end of the waveguide.

6. The sensor of claim 5, comprising an optical cone disposed in the second section with a narrow part of the optical cone facing the infrared detector inlet, such that optical irradiance on an infrared detector disposed in the detector inlet is enhanced.

7. The sensor of claim 5, comprising a reflecting mirror disposed at the second end, wherein the reflecting mirror is configured to direct energy propagating through the second section into an infrared detector oriented with an optical axis perpendicular to an optical axis of the waveguide.

8. The sensor of claim 7, wherein the reflecting mirror comprises a surface configured to scatter energy to reduce sensitivity to mechanical instability.

9. The sensor of claim 5, comprising a collimating reflector disposed at the first end, configured to collect and direct optical energy from a lamp disposed in the infrared source inlet.

10. The sensor of claim 5, comprising a reflecting mirror disposed at the first end, configured to direct optical energy from a light source having an optical axis perpendicular to an optical axis of the waveguide.

11. The sensor of claim 1, comprising at least one optical cone configured to enhance optical irradiance of an infrared detector, an infrared source, or both, disposed proximal to the first end or the second end of the wave guide.

12. The sensor of claim 1, comprising:
one or more air inlet ports disposed on at least one side of the sensor, wherein the air inlet ports are configured to allow air to enter the waveguide.

13. The sensor body of claim 1, wherein the tapered portion is towards the second end of the waveguide.

14. The sensor body of claim 1 for use with an infrared source and an infrared detector, wherein the tapered portion is narrower towards the infrared detector and wider towards the infrared source.

15. A sensor comprising:
a sensor body having a first end and an opposing second end, comprising:
a top-portion, comprising a first recess;
a bottom-portion, comprising a second recess configured to mate with the first recess;
at least one cavity providing an aperture between an outside surface of the sensor body to the first recess, to the second recess, or both;
an infrared source inlet configured to receive an infrared source; and
an infrared detector inlet configured to receive an infrared detector;
an infrared source disposed in the infrared source inlet of the sensor body;
an infrared detector disposed in the infrared detector inlet of the sensor body;
wherein, when mated, the first recess and the second recess form a waveguide configured to carry energy emitted from die infrared source to the infrared detector, the waveguide having a first section, a second section, and an intermediate section joining the first section and the second section, and
wherein the second section of the waveguide is tapered along its entire length extending between the first end of the sensor body and the opposing second end of the sensor body.

16. The sensor of claim 15, wherein the top-portion comprises a tongue or groove disposed along an outside edge of the top-portion and the bottom-portion comprises a complimentary tongue or complimentary groove disposed along an outside edge of the bottom-portion, wherein the complimentary tongue or complimentary groove is configured to mate with the tongue or the groove of the top-portion.

17. The sensor of claim 15, wherein the top-portion and bottom-portion comprise equal thicknesses measuring one half of the thickness of the sensor body.

18. The sensor of claim 15, wherein the first and second recesses are substantially similar thicknesses, thus each making up approximately one half of the waveguide, discounting any tapering within the waveguide.

19. The sensor of claim 15, comprising at least one interlocking feature configured to provide a dust and moisture barrier, align the top-portion with the bottom-portion, and eliminate lateral movement between the top-portion and the bottom-portion.

20. The sensor of claim 15, wherein the waveguide comprises a "U" shape.

21. The sensor of claim 20, wherein the infrared source is disposed at a first end of the waveguide and the infrared detector is disposed at a second end of the waveguide; and
wherein the at least one cavity is disposed between the first and second ends of the waveguide to provide airflow through natural convection of air entering through the cavity caused by thermal differences generated by the infrared source.

22. The sensor of claim 15, comprising one or more filters disposed on the outside surface over the cavity, wherein the filters are configured to block dust, moisture, or both from entering the waveguide.

23. The sensor of claim 15, comprising a printed circuit board configured to:
control activation of the infrared source,
obtain measurement data relating to energy measurements of the detector, and
provide the measurement data, analysis data relating to the measurement data, or both via one or more connector pins, wherein the sensor body is mounted to the printed circuit board via a three-point mounting system, comprising:
three mounting pass-throughs disposed in the printed circuit board;
three mounting points disposed in the sensor body, each having a screw receptacle, and
three screws configured to mount at least a portion of the printed circuit board surrounding the three mounting pass-throughs to the three mounting points, when the screws engage the screw receptacles.

24. The sensor of claim 23, wherein a portion of the sensor body is elevated above the printed circuit board when the printed circuit board and the sensor body are fully mounted.

25. A sensor, comprising:
a folded optical waveguide configured in a "U" shape having a first section having an infrared source end and a second end, an intermediate portion having a first end and a second end, a second section having a first end and an infrared detector end, the second section being tapered entirely between its first end and its infrared detector end,
wherein the second end of the first section is in contact with the first end of the intermediate portion and the first end of the second section is in contact with the second end of the intermediate portion,
wherein the waveguide is configured to convey infrared energy from the infrared source end of the first section to the infrared detector end of the second section.

* * * * *

UNITED STATES PATENT AND TRADEMARK OFFICE
CERTIFICATE OF CORRECTION

PATENT NO. : 9,804,084 B2
APPLICATION NO. : 14/077034
DATED : October 31, 2017
INVENTOR(S) : Andrian I. Kouznetsov et al.

It is certified that error appears in the above-identified patent and that said Letters Patent is hereby corrected as shown below:

In the Claims

At Column 11, Claim number 1, Line number 30, and please amend as follows:
1. A sensor, comprising:
    a sensor body having a first end and an opposing second end;
    a folded optical waveguide positioned within the sensor body and configured in a "U" shape having a first section, a second section, and an intermediate portion joining the first section and the second section, wherein the waveguide is configured to convey infrared energy from a first end of the waveguide to a second end of the waveguide, and
    wherein the second section of the waveguide is tapered along its entire length extending between the first end of the sensor body and the opposing second end of the sensor body.

Signed and Sealed this
Twenty-ninth Day of May, 2018

Andrei Iancu
*Director of the United States Patent and Trademark Office*